Figure 1:
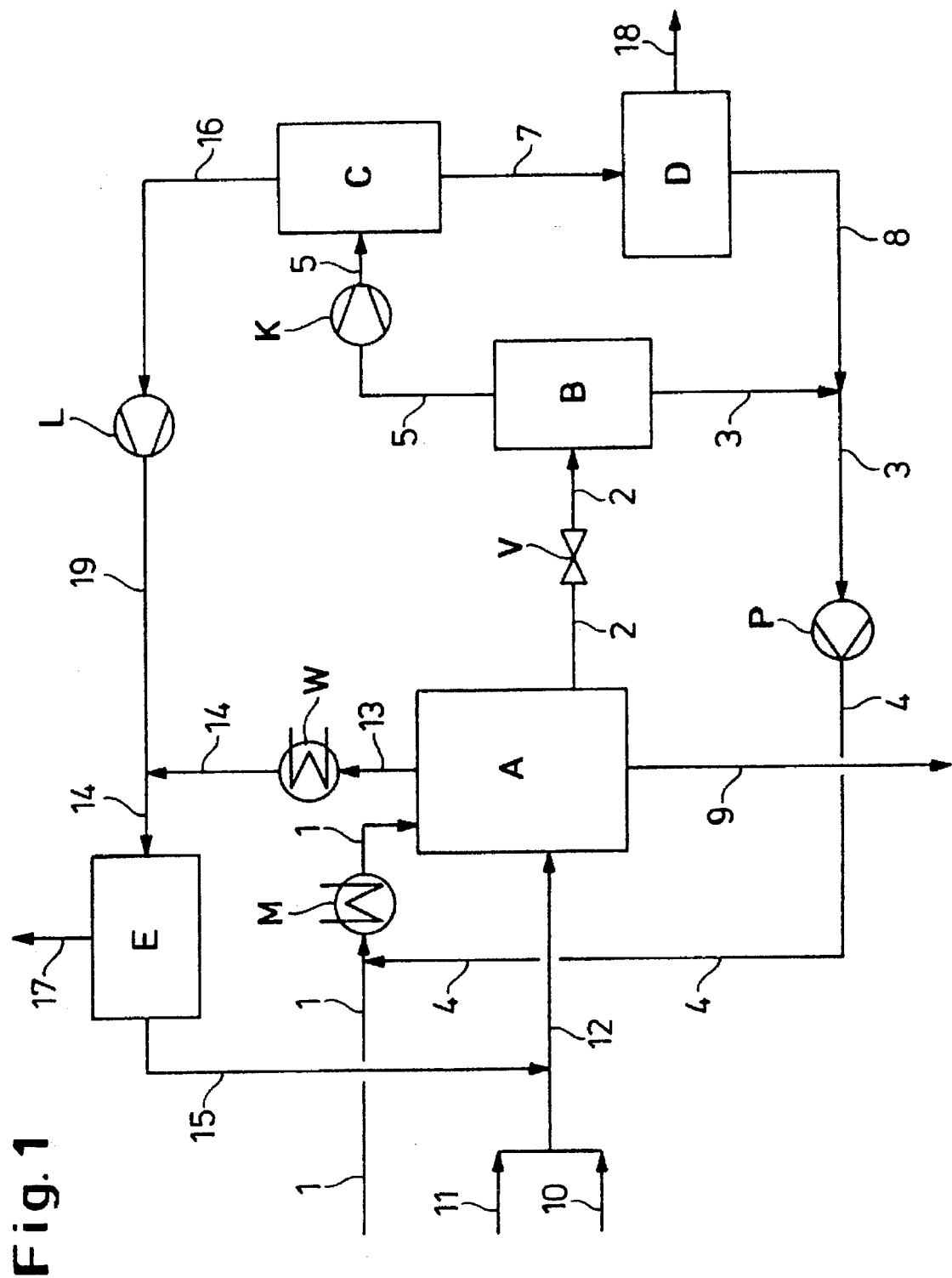

United States Patent [19]

Buysch et al.

[11] Patent Number: 5,625,091
[45] Date of Patent: Apr. 29, 1997

[54] PROCESS FOR THE PRODUCTION OF DIARYL CARBONATES

[75] Inventors: Hans-Josef Buysch; Carsten Hesse, both of Krefeld; Johann Rechner, Kempen, all of Germany

[73] Assignee: Bayer Aktiengesellschaft, Leverkusen, Germany

[21] Appl. No.: 662,431

[22] Filed: Jun. 10, 1996

[30] Foreign Application Priority Data

Jun. 23, 1995 [DE] Germany .......................... 19523390.5

[51] Int. Cl.$^6$ .................................................. C07C 68/00
[52] U.S. Cl. ........................................................ 558/274
[58] Field of Search ............................................ 558/274

[56] References Cited

U.S. PATENT DOCUMENTS 5,498,742  3/1996  Buysch et al. ...................... 558/274

FOREIGN PATENT DOCUMENTS

| 0413215 | 2/1991 | European Pat. Off. . |
| 0450442 | 9/1991 | European Pat. Off. . |
| 0450442 | 10/1991 | European Pat. Off. . |
| 0460732 | 12/1991 | European Pat. Off. . |
| 2738437 | 4/1978 | Germany . |
| 2738436 | 4/1978 | Germany . |
| 4403075 | 8/1995 | Germany . |

OTHER PUBLICATIONS

Derwent Abstract No. 78-29026A (1978), Derwent Information Ltd (London, England); DE 2738437, published Apr. 13, 1978.

Derwent Abstract No. 92-354379 (1992), Derwent Information Ltd. (London England); JP 04-257546, published Sep. 11, 1992.

Derwent Abstract No. 92-360705 (1992), Derwent Information Ltd. (London, England); JP 04-261142, published Sep. 17, 1992.

*Primary Examiner*—Johann Richter
*Assistant Examiner*—Michael G. Ambrose
*Attorney, Agent, or Firm*—Connolly & Hutz

[57] ABSTRACT

In a new process for the production of aromatic carbonates from aromatic hydroxy compound, CO and $O_2$ in contact with a platinum-group metal catalyst, a co-catalyst, a quaternary salt and a base at elevated temperature and elevated pressure, an improvement is achieved if the reaction water is removed continuously from a partial flow of the reaction under reduced pressure and largely isothermal conditions and the dehydrated partial flow is again supplied to the reaction.

6 Claims, 4 Drawing Sheets

PROCESS FOR THE PRODUCTION OF DIARYL CARBONATES

The present invention relates to a process for the production of diaryl carbonates by reaction of an aromatic hydroxy compound (eg, phenol) with carbon monoxide and oxygen in the presence of a catalyst, a co-catalyst, a quaternary salt and a base, said process being characterised in that the reaction water is removed continuously by a partial flow of the reaction solution being constantly withdrawn from the reactor, by removing the water at reduced pressure under largely isothermal conditions and by then feeding the reaction solution back.

It is known to produce organic carbonates by oxidative reaction of an aromatic hydroxy compound with carbon monoxide in the presence of a noble-metal catalyst (DE-OS 27 38 437). By way of noble metal use is preferably made of palladium. In addition, a co-catalyst (eg, manganese salts or cobalt salts), a base, a quaternary salt, various quinones or hydroquinones and drying agents can be employed. In this process working may take place in a solvent, preferably methylene chloride.

In the course of the reaction of aromatic hydroxy compounds with carbon monoxide and oxygen one mol of water is liberated per mol of organic carbonate formed. If this water remains in the reaction system, organic carbonate that has already formed can be hydrolysed, so that only low space-time yields can be achieved without effective separation of water. In addition, the catalyst system can be deactivated by water. Reactivation of the deactivated catalyst requires great technical effort. Replacement of the deactivated catalyst is associated with high costs. For these reasons, effective removal of water is essential for economic utilisation of this process.

In DE-OS 27 38 437 the addition of molecular sieve is proposed with a view to the separation of water. But the use of molecular sieve makes technical utilisation of the process unattractive, since for effective separation of the water from the liquid phase large quantities of molecular sieve (100–500% excess) are required which have to be regenerated with great technical effort.

In EP 450 442 the use of carbon dioxide as drying agent is proposed. With a view to drying the reaction system, about 30–35% carbon dioxide is added to the reaction gas, which consists of oxygen and carbon monoxide. This process has two substantial disadvantages: as a result of dilution of the reaction gas the space-time yield is drastically reduced. Furthermore, in the course of circulation of the reaction gas, as required by the technical realisation of this process, an enrichment of the carbon dioxide in the gas flow has to be prevented by means of elaborate processes. This requires considerable effort as regards apparatus and associated high costs, making economic utilisation of this process impossible.

In JP-04 257 546 a process is described in which organic carbonates are produced by oxidative reaction of an aromatic hydroxy compound with carbon monoxide in the presence of a noble-metal catalyst and a quaternary salt with an iodide anion by continuous feeding into a distillation column at 150°–205° C. and 30–50 bar. The reaction water is distilled off continuously. One disadvantage with this process is that, with a view to removing the reaction water, working has to take place in a distillation column which, by virtue of its design, makes only short dwell-times possible. The space-time yields that can be achieved with this process are accordingly very low at only 17.8 g/l·h. Associated with the implementation of the reaction in a distillation column is the use of large quantifies of halides at high temperatures (150°–205° C.). This results in considerable corrosion problems which additionally necessitate considerable expense as regards apparatus. Those skilled in the art also know that under the specified reaction conditions the iodide that is preferably employed is not stable and is oxidised to iodine to a considerable degree. This results in considerable losses of the quaternary salt and the formation of by-products, greatly impairing the selectivity and hence the economy of this process. In addition, at these high temperatures and pressures a rapid deactivation of the homogeneous catalyst system, caused by the losses of halogen and the growth of particles of palladium, is to be reckoned with, so that economic utilisation of this process is not possible.

In JP-04 261 142 a process is described in which working is effected as in JP-04 257 546 but with the difference that with a view to increasing the dwell-time additional reactors have been attached to the distillation column. The problems cited above of corrosion, catalyst deactivation and the loss of quaternary salt, as well as the associated side-reactions, are also not resolved in this application. The proposed apparatus also offers no advantages in any other respect. Although the dwell-time is increased by means of the additional reactors, the proposed design results in considerable back-mixing within the apparatus, so that side-reactions are able to proceed to an increased extent, as a result of which the selectivity of 99% (JP-04 257 546) diminishes to 97% (JP-04 261 142). As a result of the reactors that have been additionally attached, effective removal of the reaction water is impossible, for the reaction water that is formed in the reactors is only removed in the distillation column subsequently, so that carbonate formed in the reactors is again dissociated hydrolytically. The space-time yields that can be achieved with JP-04 261 142 are therefore, once again, clearly lower at about 9 g/l·h than in the case of JP-04 257 546, so that economical utilisation of this process is also not possible.

The object was therefore to find a process permitting synthesis of aromatic carbonates to be carried out subject to continuous removal of the reaction water arising, with a high space-time yield, under economic, technically achievable and reproducible conditions.

It has now been found that the disadvantages described can be overcome if a partial flow is continuously withdrawn from the reactor, the pressure of said partial flow is lowered, the reaction water is removed under largely isothermal conditions and under reduced pressure and then the reaction solution that has been dehydrated in this way is continuously supplied to the reactor again. Surprisingly, the catalyst system suffers no damage in the course of this release of pressure or application of vacuum.

Accordingly the invention relates to a process for the production of an aromatic carbonate of the formula

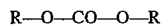

$$R-O-CO-O-R \qquad (I)$$

in which

R signifies substituted or non-substituted $C_6$–$C_{12}$ aryl, preferably substituted or non-substituted phenyl, and particularly preferably non-substituted phenyl, by reaction of an aromatic hydroxy compound of the formula

$$R-O-H \qquad (II)$$

in which R has the significance specified above,
with carbon monoxide and oxygen in the presence of a platinum-group metal catalyst, a co-catalyst, a quaternary salt and a base at a temperature of 30° to 200° C., preferably 30° to 150° C., particularly preferably 40° to 120° C., and a pressure of 1 to 200 bar, preferably 2 to 100 bar, particularly preferably 5 to 50 bar, said process being characterised in that the reaction water is continuously removed from a partial flow of the reaction solution under reduced pressure and largely isothermal conditions and the dehydrated partial flow is supplied to the reaction again.

In the process according to the invention the water contained in the educts and the water arising continuously as a result of the reaction is removed by withdrawal of a partial flow of the reaction solution, said partial flow firstly being relieved of pressure, then dehydrated by evaporation of the water, largely isothermally at reduced pressure, and then supplied to the reactor again.

The partial flow of reaction solution withdrawn per hour may amount in the process according to the invention to 0.01 to 30 times, preferably 0.05 to 20 times, and particularly preferably 0.1 to 10 times, the contents of the reactor.

Evaporation of the water may be effected in types of apparatus known to those skilled in the art, for example in vertical-pipe, horizontal-pipe, slanting-pipe, rotor or thin-layer, centrifugal, worm and falling-film evaporators, in tube-bundle evaporators, basket evaporators, evaporators with external return pipe and forced circulation, evaporators with external heating elements and forced circulation and other evaporators known to those skilled in the art (P. Grassman, F. Widmer, Einführung in die thermische Verfahrenstechnik, Walter de Gruyter, Berlin, N.Y. 1974); furthermore, simple distillation and rectifying columns with accompanying heating elements are also suitable; use should preferably be made of thin-layer and falling-film evaporators and evaporators with forced circulation and heating elements located internally or externally.

In another embodiment the removal of water can be brought about by spontaneous evaporation in the course of the relief of pressure to a reduced value; in the process the partial flow withdrawn cools down and has to be heated to reaction temperature again prior to being recirculated.

The process according to the invention for the formation of carbonate is implemented at a reaction temperature of 30° to 200° C., preferably 30° to 150° C., particularly preferably 40° to 120° C., and at a reaction pressure of 1 to 200 bar, preferably 2 to 100 bar, particularly preferably 5 to 50 bar. With a view to the removal of water in the process according to the invention a temperature is adjusted which lies within the range of up to ±30° C., preferably up to ±20° C., and particularly preferably up to ±10° C., of the reaction temperature. The pressure for the removal of water is around 1 to 5,000 mbar, preferably 2 to 3,000 mbar, and particularly preferably 5 to 1,000 mbar.

In the preferred embodiment all pipelines and evaporators are heated in such a way that the reaction solution withdrawn remains largely at the temperature of the contents of the reactor.

By means of a separating device located in the exit-gas flow of the dehydration stage, such as a fractionating column, a distillation column with plates or packing and other types of apparatus known to those skilled in the art, most of the educts (eg, phenol) entrained in the course of dehydration and products can be separated from the water and conducted into the return flow to the reactor. The separated mixture consisting of water and entrained educts or products can be separated in accordance with the state of the art—for example, by extraction or distillation.

The portion of dissolved gases expelled with the mixture consisting of water and entrained educts or products may, in a preferred embodiment, be supplied again after the separation to the recycled gas of the reactor. The separation of entrained educts (eg, phenol), products and water from the gaseous mixture, which is optionally compressed prior to the separation, to be recycled is effected in accordance with the state of the art—for example, by adsorption, absorption or preferably by condensation. The reaction gas required for the reaction, consisting of carbon monoxide, oxygen and an inert gas, is introduced for this purpose in a quantity of 1 to 10,000 Nl per liter of reaction solution, preferably 5 to 5,000 Nl per liter of reaction solution, and particularly preferably 10 to 1,000 Nl per liter of reaction solution. With regard to the stated volumes the gas originating from the dehydration stage that is to be recycled is taken into account with respect to its proportions of CO and $O_2$.

The composition of the reaction gases carbon monoxide and oxygen can be varied within wide concentration limits, but a $CO:O_2$ molar ratio (standardised to CO) is expediently adjusted of 1:(0.001–1.0), preferably 1:(0.01–0.5) and particularly preferably 1:(0.02–0.3). With these molar ratios the partial pressure of oxygen is sufficiently large to be able to achieve high space-time yields and at the same time to be incapable of forming any explosive gaseous mixtures of carbon monoxide and oxygen. The reaction bases are not subject to any particular purity requirements. Hence synthesis gas can serve as CO source and air can serve as $O_2$ carrier, but care should be taken to ensure that no catalyst poisons such as sulphur or the compounds thereof are introduced. In the preferred embodiment of the process according to the invention use is made of pure CO and pure oxygen.

Inert constituents of the reaction gases in the process according to the invention may be nitrogen, hydrogen, carbon dioxide, noble gases and also organic compounds which are stable under reaction conditions and which form an azeotrope with water. The concentration of inert gas in the reaction gas may amount to 0 to 60 vol-%, preferably 0 to 20, and particularly preferably 0 to 5 vol-%. The concentration of 0 vol-% represents the special case of the preferred state which is free of inert gas.

The aromatic hydroxy compounds that can be caused to react in accordance with the invention are, for example, phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and Bisphenol A, preferably phenol. In the case of substitution of the aromatic hydroxy compound it is generally a question of 1 or 2 substituents in respect of $C_1$–$C_4$-alkyl, $C_1$–$C_4$-alkoxy, fluorine, chlorine or bromine.

Bases that can be used in the process according to the invention are alkali salts of aromatic hydroxy compounds of the formula (II) in which R has the significance specified above. Particularly preferred is the use of an alkali salt of the aromatic hydroxy compound that is also to be caused to react so as to form the organic carbonate. These alkali salts may be lithium, sodium, potassium, rubidium or caesium salts. Use is preferably made of lithium, sodium and potassium phenolates, particularly preferably sodium phenolate.

The alkali-metal phenolate may be added to the reaction mixture as a pure compound in solid form or as a melt. Of course, the hydrates of the alkali-metal phenolates can also be used in the process according to the invention. As an example of such a hydrate, mention may be made here, without restricting the scope of the process according to the invention, of sodium phenolate trihydrate. However, the quantity of added water is preferably such that a maximum of 5 mol of water are used per mol of base. Higher concentrations of water generally result in inferior conversions and decomposition of carbonates formed. In another embodiment of the invention the alkali-metal phenolate is added to the reaction mixture as a solution which contains 0.1–80 wt-%, preferably 0.5–65 wt-%, and particularly preferably 1–50 wt-%, of the alkali-metal phenolate. By way of solvent in this process use may be made of alcohols or phenols, such as the phenol to be reacted, and also inert solvents. Those inert solvents mentioned below by way of reaction media may be referred to. These solvents may be used on their own or in any combination with one another. Thus one embodiment of the process according to the invention consists, for example, in that the base is dissolved in a phenol melt that has been diluted with an inert solvent. The base is preferably dissolved in the melt of an aromatic hydroxy compound. Particularly preferably, the base is dissolved in a melt of the aromatic hydroxy compound that is to be caused to react so as to form the organic carbonate. More particularly the base is added when dissolved in phenol. The base is added in a quantity that is independent of the stoichiometry. The ratio of platinum-group metal—eg, palladium—to base is preferably chosen to be such that use is made of 0.1 to 500, preferably 0.3 to 200, and particularly preferably 0.9 to 130, equivalents of base per gram atom of platinum-group metal—eg, palladium.

The process according to the invention is preferably implemented without solvent. Of course, inert solvents may also be used. By way of examples of solvents mention may be made of dimethyl acetamide, N-methyl pyrrolidone, t-butanol, cumyl alcohol, isoamyl alcohol, tetramethyl urea, diethylene glycol, halogenated hydrocarbons (eg, chlorobenzene or dichlorobenzene) and ethers such as dioxane, tetrahydrofuran, t-butyl methylether and etherified glycols.

The platinum-group metal catalysts that are suitable for the process according to the invention consist of at least one noble metal pertaining to Group VIII, preferably palladium. With the process according to the invention it may be added in various forms. Palladium may be employed in metallic form or preferably in the form of palladium compounds with degrees of oxidation 0 and +2, such as palladium(II) acetylacetonate, palladium(II) halides, palladium(II) carboxylates pertaining to $C_2$–$C_6$ carboxylic acids, palladium (II) nitrate, palladium(II) oxides or palladium complexes which may contain, for example, olefins, amines, phosphines and halides. Particularly preferred are palladium bromide and palladium acetylacetonate.

The quantity of platinum-group metal catalyst is not limited in the process according to the invention. Preferably so much catalyst is added that the concentration of the metal in the reaction charge amounts to 1–3,000 ppm, concentrations of 5–500 ppm being particularly preferred.

By way of co-catalyst for the process according to the invention use is made of a metal pertaining to Groups III A, III B, IV A, IV B, V B, I B, II B, VI B, VII B, the rare-earth metals (atomic numbers 58–71) or to the iron group of the Periodic System of Elements (Mendeleev), it being possible for use to be made of the metal in various degrees of oxidation. Use is preferably made of Mn, Cu, V, Zn, Ce and Mo. Without restricting the scope of the invention, mention may be made of manganese(II), manganese(III), copper(I), copper(II), cobalt(II), cobalt(III), vanadium(III) and vanadium(IV). The metals may be employed, for example, in the form of halides, oxides, carboxylates of $C_2$–$C_6$ carboxylic acids, diketonates or nitrates and also in the form of complex compounds which may contain, for example, carbon monoxide, olefins, amines, phosphines and halides. Particularly preferred is the use of Mn, Cu, Mo and Ce. The use of manganese compounds is most preferred in the process according to the invention, in particular manganese (II) complexes, with manganese(II) acetylacetonate or manganese(III) acetylacetonate being particularly preferred.

The co-catalyst is added in such a quantity that its concentration lies within the range from 0.0001 to 20 wt-% of the reaction mixture, with the concentration range from 0.005 to 5 wt-%, particularly 0.01 to 2 wt-%, being preferred.

The quaternary salts employed in the context of the present invention may be, for example, ammonium, phosphonium or sulphonium salts that are substituted with organic residues. Suitable for use in the process according to the invention are ammonium, phosphonium and sulphonium salts that bear by way of organic residues $C_6$ to $C_{10}$ aryl, $C_7$ to $C_{12}$ aralkyl and/or $C_1$ to $C_{20}$ alkyl residues and by way of anion a halide, tetrafluoroborate or hexafluorophosphate. In the process according to the invention use is preferably made of ammonium salts that bear by way of organic residues $C_6$ to $C_{10}$ aryl, $C_7$ to $C_{12}$ aralkyl and/or $C_1$ to $C_{20}$ alkyl residues and by way of anion a halide, tetrabutyl ammonium bromide being particularly preferred. The quantity of such a quaternary salt may amount, for example, to 0.1–20 wt-%, relative to the weight of the reaction mixture. This quantity preferably amounts to 0.5–15 wt-%, particularly preferably 1–5 wt-%.

Prior to being used in the process according to the invention the platinum-group metal catalyst is preferably activated. To this end the platinum-group metal compound is preferably so selected that its concentration in the activation charge amounts to 0.0001 to 30 wt-%, particularly preferably 0.001 to 10 wt-%, and it is dissolved in an inert solvent or directly in the melt of the aromatic hydroxy compound or mixtures of the same. The aforementioned quaternary salt is added to this solution. This solution is then treated with carbon monoxide at 15° to 200° C., preferably at 20° to 150° C., and particularly preferably at 40° to 100° C. This may be done both by carbon monoxide being introduced at normal pressure in a quantity amounting to 0.1 to 250 l/h, preferably 0.5 to 200 l/h, and particularly preferably 1 to 100 l/h, per gram of the platinum-group metal employed and also by mixing the solution with carbon monoxide in an autoclave under a pressure of 1 to 300 bar, preferably 1 to 200 bar, and particularly preferably 1–150 bar. The activation period depends on the platinum-group metal catalyst used and on an inert solvent that is optionally employed. In general it ranges from just a few minutes to a few hours. The platinum-group metal catalyst may be activated directly prior to the reaction, but it may also be activated after separation of the solvent or of the aromatic hydroxy compound—for example, by being distilled off, isolated in activated form and stored.

In another preferred embodiment, instead of the homogeneous catalyst system use is made of heterogeneous catalysts in which the platinum-group metal or the platinum-group metal and the co-catalyst are applied onto a heterogeneous support and used in the form of powder or moulded body. The remaining components of the catalyst system, such as the base, the quaternary compound and, optionally, the co-catalyst, are moreover dissolved homogeneously in the reaction solution. The quantity of the platinum-group metal with respect to the overall weight of the heterogeneous catalyst amounts to 0.01 to 15 wt-%, preferably 0.05 to 10 wt-%, reckoned as platinum-group metal.

By way of co-catalysts on the catalyst support use is made of at least one metal compound of the type specified above.

The quantity of the co-catalyst with respect to the overall weight of the heterogeneous catalyst amounts to 0.01 to 15 wt-%, preferably 0.05 to 10 wt-%, reckoned as metal.

Suitable by way of catalyst support are one or more metal oxides selected from the group comprising V, Mn, Ti, Cu, Zr, La, the rare-earth metals (atomic numbers 58–71), both in the sense of chemically homogeneous pure substances and in a mixture, and also iron oxides and cobalt oxides, nickel oxide, aluminium oxide, silicon oxide and magnesium oxide, zeolites and activated carbons. If the supported catalyst is used in the form of powder, then with a view to mixing the reaction components the stirrer vessels to be used are equipped with stirrers that can be used for this purpose or they are designed as bubble-column reactors.

In the course of working with supported-catalyst powders in the form of a suspension in stirrer vessels or bubble columns, quantities from 0.001 to 50 wt-%, preferably from 0.01 to 20 wt-%, and particularly preferably from 0.1 to 10 wt-%, of supported-catalyst powder are used, in relation to the quantity of aromatic hydroxy compound employed.

In particularly preferred embodiments the heterogeneous supported catalyst is employed fixed in stirrer vessels, bubble columns, a trickle-phase reactor or cascades of these reactors. Separation of the supported catalyst is then dispensed with entirely.

The production of aromatic carbonates with the platinum-group-metal supported catalysts according to the invention may be effected discontinuously or continuously. In the case of a continuous procedure in counterflow or concurrent flow or in the trickle phase on the fixed-bed catalyst, loads are adjusted of 0.01 to 20 g of aromatic hydroxy compound per gram of supported catalyst per hour, preferably 0.05 to 10 g of aromatic hydroxy compound per gram of supported catalyst per hour, and particularly preferably 0.1 to 5 g of aromatic hydroxy compound per gram of supported catalyst per hour.

Suitable by way of reactors for the process according to the invention with homogeneous or heterogeneous catalyst are stirrer vessels, autoclaves and bubble columns, it being possible for these to be employed as individual reactors or as a cascade. In a cascade 2 to 15, preferably 2 to 10, and particularly preferably 2 to 5, reactors may be connected in series.

With a view to mixing the reaction components the stirrer vessels to be used in accordance with the invention are equipped with stirrers that can be used for this purpose. Such stirrers are known to those skilled in the art. By way of examples mention may be made of: disk, impeller, propeller, paddle, multi-stage impulse counter-current and intermediate multi-stage impulse counter-current stirrers, tubular stirrers and various types of hollow stirrer. Preferred stirrers are those which permit effective mixing of gases and liquids, for example hollow-tube gassing stirrers, propeller stirrers, etc.

By way of bubble columns the following types may be used in the process according to the invention: simple bubble columns, bubble columns with baffles such as: bubble columns with parallel chambers, cascade bubble columns with sieve plates or single-hole plates, bubble columns with packings, with static mixers, pulsating sieve-plate bubble columns, loop reactors such as: mammoth loop reactors, downflow loop reactors, jet loop reactors, free-jet reactors, jet-tube reactors, bubble columns with liquid-immersion emitters, downflow–upflow bubble columns and other bubble-column reactors known to those skilled in the art (Chem. Ing. Tech. 51 (1979) No. 3, pp 208–216; W. D. Deckwer, Reaktionstechnik in Blasensäulen, Otto Salle Verlag 1985).

In a preferred embodiment use is made of bubble-column reactors and bubble-column cascades that permit effective mixing of gas and liquids, such as cascade bubble columns and loop reactors. With a view to maintaining good, thorough mixing of liquid and reaction gas, distributing and redispersing devices may be attached along the longitudinal axis of the bubble-column reactors. By way of fixed redispersing devices use may be made of single-hole plates, perforated plates, sieve plates and also other baffles known to those skilled in the art. For the initial dispersion of the reaction gas in the liquid phase in the course, of charging, use may be made of conventional devices such as porous sintered plates, perforated plates, sieve plates, plug-in tubes, nozzles, gassing rings and other dispersing devices known to those skilled in the art.

The process according to the invention may be implemented in various embodiment variants. One possibility is discontinuous implementation. In this process CO and oxygen are conducted into the reaction mixture by means of either a gassing stirrer, in the case of a stirrer vessel, or other known gas-distributing devices. After the optimal conversion has been attained the reaction mixture is removed from the reactor, or processing is optionally effected within the reactor. In the case of the use of supported catalysts in powder form these may be separated from the reaction mixture, for example by filtration, sedimentation or centrifugation.

Supported catalysts employed in discontinuous trials may be used repeatedly in the case of identical feed materials, optionally without cleaning. In the case of a continuous mode of operation the supported catalysts employed may remain in the reactor over a long period and may optionally be regenerated.

A continuous mode of operation in the individual reactor or in a cascade of several reactors is preferably employed. In the case of the use of fixed heterogeneous catalysts these may remain in the reactor over a long period and may also optionally be regenerated there.

In FIG. 1 the mode of operation is represented with only one reactor by way of example, wherein the mode of operation according to the invention is not to be regarded as being restricted to this example. The preferred embodiment of the process according to the invention consists in that the platinum-group metal catalyst is activated in the manner described above and this solution is then added continuously to the reactor (A), at the same time as other solutions which contain the remaining components of the reaction system in the concentrations specified above, via line 1. By means of a heater element (M) connected in series upstream the liquid reaction components can be preheated to the specified reaction temperature. Optionally it may be advantageous to dose the base that is necessary for the reaction separately. A partial flow of the contents of the reactor is supplied to the evaporator (B) continuously via line 2 and the relief valve (V). The dehydrated solution is supplied to the reactor again via line 3, the pump (P) and line 4, either directly or via line 1 and the heater element (M). The water-phenol mixture that is evaporated in the vacuum leaves the evaporator (B) via line 5 and is condensed again with the aid of the condenser (K); in the separator (C) the water-phenol mixture is separated from the entrained reaction gas which is supplied via line 16 to the compressor (L) and line 19 to the $CO_2$ separation stage (E). The water-phenol mixture reaches the water-phenol separation stage (D) via line 7. Via line 8 recovered phenol is supplied to the evaporator outlet 3 and the separated water is transferred out via line 18. Carbon monoxide and oxygen reach the reactor (A) via lines 10 and 11 respectively and line 12. In the process CO and oxygen, in the quantifies specified above, are conducted into the reaction mixture by means of either a gassing stirrer, in the case of a stirrer vessel, or other known gas-distributing devices. Excess reaction gas leaves the reactor via line 13, is freed from entrained phenol with the aid of the condenser (W) and reaches the $CO_2$ separation stage (E) via line 14. Via line 15 excess reaction gas together with the feed gas reaches the reactor (A) again. $CO_2$ is transferred out via line 17. The reaction product is withdrawn via line 9 and supplied for processing. The filling-level is regulated in the continuously operated reactor in accordance with known methods.

In the case of the use of a cascade of reactors (FIGS. 2 and 3, here represented by way of example with three reactors in each case) the liquid reaction components described above are charged into the first reactor (A) and may optionally be preheated to the specified reaction temperature in a heater element (M) connected in series upstream. They are introduced in liquid form via line 1 preferably at the upper end of the reactor. The liquid phase to be withdrawn from the respective reactors is withdrawn at the lower end of the reactor and again charged via the lines 2 and 3 respectively into the following reactor in each case, at the upper end. At the last reactor the flow of product is withdrawn (line 4 in FIGS. 2 and 3) and supplied for processing. The desired filling-level in the continuously operated reactors is regulated in accordance with known methods. The dehydration in accordance with the invention may be effected at each cascade reactor, it being possible for feedback of the phenol to be effected into each individual reactor or preferably into the first reactor. Feedback of the dehydrated reaction solutions is preferably effected into the respective reactor, less preferably into the first reactor. The phenol-water condensation and subsequent separation into phenol and water can be effected at each individual reactor or preferably centrally in a single aggregate. The feedback of gas from the water-separation stage described above can also be effected centrally, together with the recycled gas and the supplementary gas.

Figure 2:
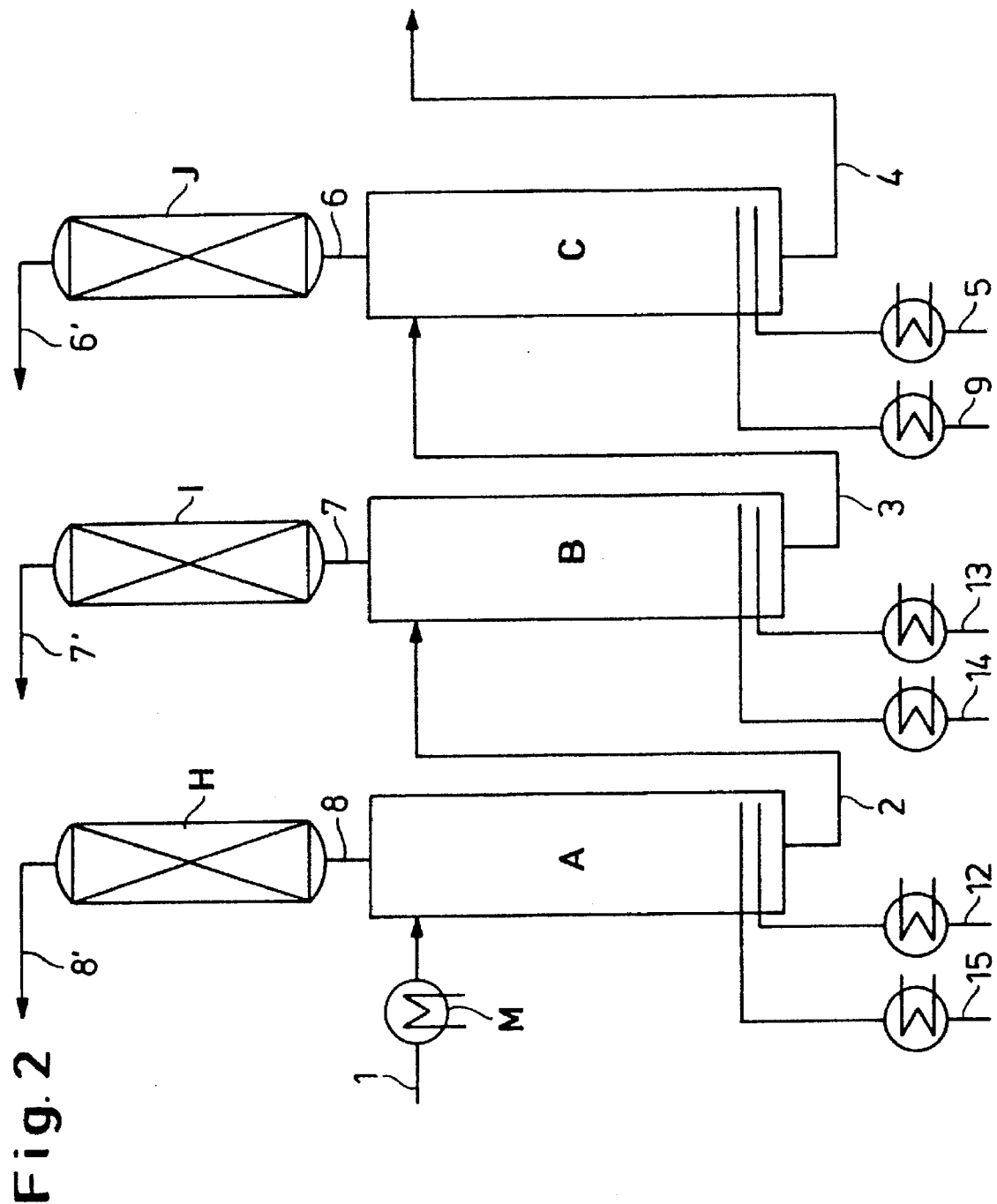
Figure 3:
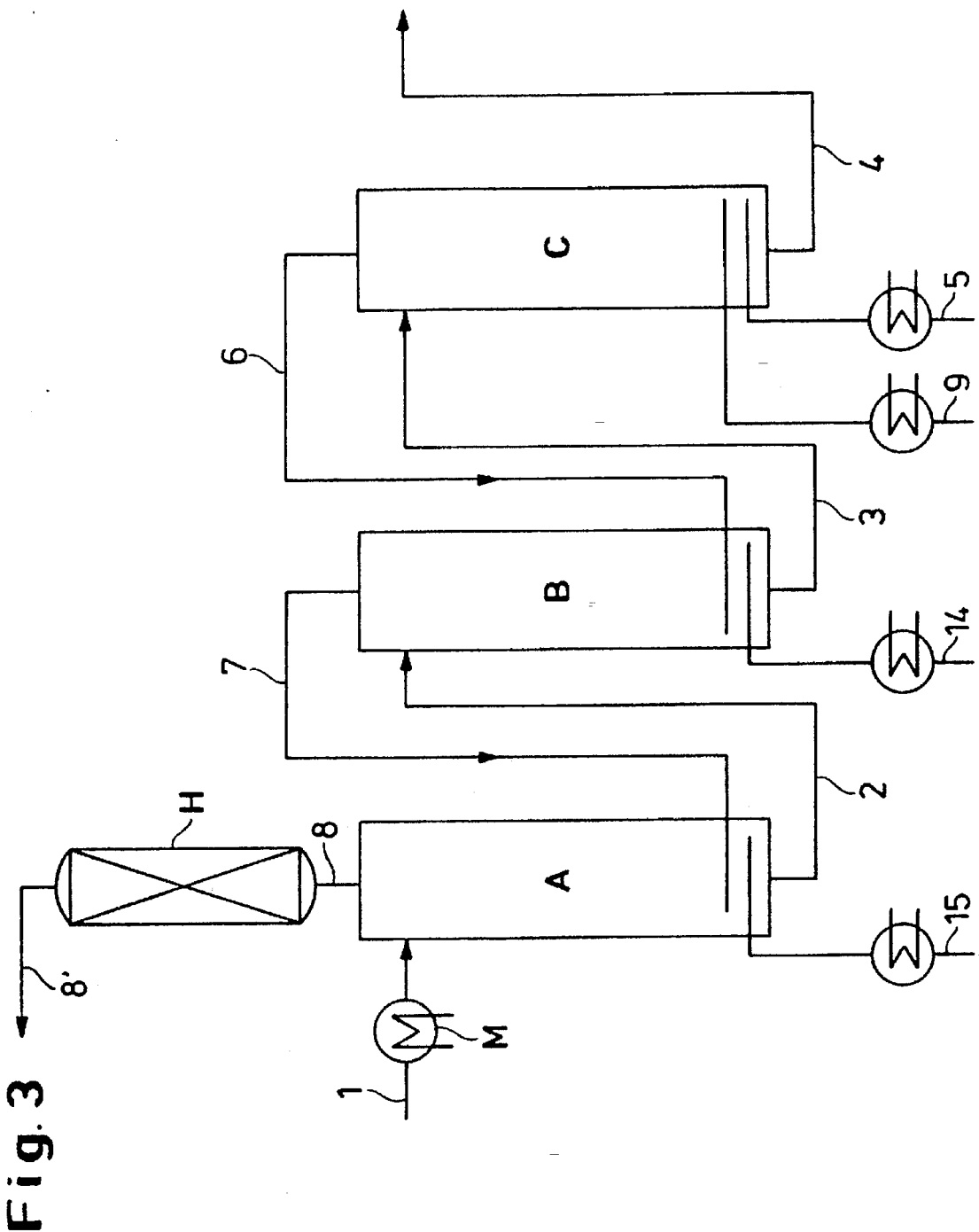

In the case of the use of a cascade the gas phase can be sent through the continuously running flow of liquid either in crossflow (FIG. 2) or in counterflow (FIG. 3). For the sake of better comprehensibility, in these Figures the process according to the invention for the separation of water has not been drawn in, so as to be better able to clarify the application of crossflow and counterflow. By this means, further variants of the process according to the invention are to be described, without, however, restricting it to these variants.

In this connection crossflow mode of operation of the cascade means that the reaction gases are charged via the lines 12, 15, 13, 14, 9 and 5 (FIG. 2) and in each case are withdrawn again at the upper end of each reactor via the lines 8, 7 and 6 (FIG. 2) together with the entrained educt (II)—ie, the reaction gas flows through the reactors transversely in relation to the direction of flow of the liquid phase. In the separating devices (H), (I) and (J) the educt (II) is separated and returned into the respective reactors. Via the lines 8', 7' and 6' the excess reaction gas leaves the reactor and is again supplied to the reactors (A), (B) and (C) after the $CO_2$ separation stage and also the replacement of the consumed reaction gas. In this connection the replenishment of $O_2$ may be effected centrally or via the lines 15, 14 and 9, it being possible for the overall quantity of the charged oxygen to be distributed arbitrarily to the individual reactors. Similarly, the overall quantity of the carbon monoxide charged can be distributed arbitrarily to the individual reactors. By this means, in contrast to the overall cascade, the counterflow mode of operation of liquid phase and gas phase is achieved in each individual reactor.

Counterflow mode of operation of the cascade (FIG. 3) means that the gas phase is charged into the last reactor (C), conducted continuously, in the opposite direction to the liquid phase running from the first reactor (A) to the last reactor (C), through the lines 6 and 7 (FIG. 3) and introduced again at the lower end, in each case, of the reactors (B) and (A) respectively. The dosing, and guiding of the liquid phase in the reactors is identical with the crossflow mode of operation. At the upper end of the first reactor (A) the excess reaction gas is withdrawn together with entrained educt (II) via line 8. In the separating device (H) the educt (II) is separated and returned into the reactor (A). Via the line 8' the excess reaction gas leaves the reactor and is again supplied to the reactor (C) after the $CO_2$ separation stage and also the replacement of the consumed reaction gas. In order to ensure a constant $O_2$ content it can be expedient to introduce oxygen, separately from the carbon monoxide, into the reactors via the lines 14, 15 and 9, it being possible for the overall quantity of the oxygen charged to be distributed arbitrarily to the individual reactors.

The embodiments described in FIGS. 1–3 by way of examples with reference to bubble columns may be taken to relate equally, without restriction, to a stirrer vessel or a cascade of stirrer vessels with suitable stirring devices.

Processing of the liquid reaction product is effected in accordance with the state of the art by filtration, distillation and crystallisation. The recovered catalyst components are recycled, inasmuch as constituents that have been transferred out are replenished and the catalyst components in active form are again supplied to the reactor (A), together with circulating phenol and fresh phenol.

The following Examples elucidate the process according to the invention, without, however, restricting it to them.

EXAMPLE 1

In an autoclave (11) with gassing stirrer, condenser and cold trap which is connected in series downstream and also an evacuation line with deep-freeze traps that is capable of being connected, 0.34 g palladium bromide and 8.31 g tetrabutyl ammonium bromide were dissolved at 80° C. in 450 g phenol. Carbon monoxide was conducted through this solution for one hour (3 l/h) with a view to activation of the catalyst. Then 0.77 g manganese(II) acetylacetonate and 2.21 g sodium phenolate, dissolved in 50 g phenol, were added and, subject to introduction of a gaseous mixture consisting of carbon monoxide and oxygen (96.5:3.5 vol-%), the pressure was adjusted to 10 bar. The quantity of gaseous mixture consisting of carbon monoxide and oxygen was adjusted to 80 Nl/h. Every hour a sample was withdrawn from the reaction mixture and analysed by gas chromatography. After the sampling the pressure of the autoclave was lowered with a view to removal of water, the dosing of the gases was shut off by closure of the valves and a vacuum of 20 mbar was applied for 5 min, then the pressure was raised again to 10 bar with the mixture of carbon monoxide and oxygen and the reaction was continued as described above. This cycle was repeated three times altogether.

Analyses showed that after one hour 7.6% diphenyl carbonate, after 2 hours 12.4% diphenyl carbonate and after 3 hours 17.7% diphenyl carbonate was contained in the reaction mixture. In the deep-freeze traps of the vacuum line 22.7 g of a phenol/water mixture were condensed.

COMPARATIVE EXAMPLE

The experiment was repeated as described in Example 1, but the evacuation cycles for the removal of water were dispensed with.

The analyses of the samples by gas chromatography showed that after one hour 4.7% diphenyl carbonate, after 2 hours 5.9% diphenyl carbonate and after 3 hours 6.4% diphenyl carbonate was contained in the reaction mixture. In the cold trap behind the condenser 0.2 g of a phenol/water mixture was condensed.

EXAMPLE 2

The experiment was repeated as described in Example 1, but instead of 0.34 g use was made of only 0.08 g $PdBr_2$.

The analyses showed that after one hour 7.3% diphenyl carbonate, after 2 hours 12.2% diphenyl carbonate and after 3 hours 17.1% diphenyl carbonate was contained in the reaction mixture. In the deep-freeze traps of the vacuum line 26.0 g of a phenol/water mixture were condensed.

EXAMPLE 3

Example 1 was repeated, whereby instead of 0.34 g $PdBr_2$ use was made of 0.10 g palladium acetylacetonate. Manganese(II) acetylacetonate was added prior to activation of the palladium.

The analyses showed that after one hour 8.5% diphenyl carbonate, after 2 hours 13.2% diphenyl carbonate and after 3 hours 18.5% diphenyl carbonate was contained in the reaction mixture. In the deep-freeze traps of the vacuum line 24.9 g of a phenol/water mixture were condensed.

EXAMPLE 4

Example 1 was repeated, whereby instead of 0.34 g use was made of only 0.08 g palladium bromide. Manganese(II) acetylacetonate was added prior to activation of the palladium.

The analyses showed that after one hour 8.1%, diphenyl carbonate, after 2 hours 13.4% diphenyl carbonate and after 3 hours 18.7% diphenyl carbonate was contained in the reaction mixture. In the deep-freeze traps of the vacuum line 25.4 g of a phenol/water mixture were condensed.

EXAMPLE 5

Coating of a Powdery Titanium Dioxide with Palladium and Manganese

To a suspension of 283.5 g titanium-oxide powder (Norton) in 1,500 ml water there were added at room temperature 300 ml of a solution of 40.5 g (0.16 mol) manganese(II)-nitrate-4-hydrate in water. Then the mixture was made alkaline with diluted caustic soda solution. The suspension was drawn off by suction, washed with water, dried at 100° C. and annealed for 3 h at 300° C. The support doped with manganese was suspended in 1500 ml water and mixed with 300 ml of a solution containing 50 g sodium tetrachloropalladate(II) solution with 15% palladium. Then the mixture was made alkaline with diluted caustic soda solution. The suspension was drawn off by suction, washed and dried at 100° C.

The catalyst contained 2.5% Pd and 3% Mn, in each case reckoned as metal.

Use of the Supported Catalyst for the Production of Diphenyl Carbonate

Example 1 was repeated, whereby instead of 0.34 g palladium bromide use was made of 4 g of the heterogeneous catalyst produced above and working was effected at 8 bar.

The analyses showed that after one hour 7.5% diphenyl carbonate, after 2 hours 12.5% diphenyl carbonate and after 3 hours 16.5% diphenyl carbonate was contained in the reaction mixture. In the deep-freeze traps of the vacuum line 23.7 g of a phenol/water mixture were condensed.

EXAMPLE 6

Coating of a Powdery Titanium Dioxide with Palladium and Cobalt

To a solution of 18.75 g palladium(II) bromide (0.07 mol), 28.5 g sodium bromide (0.28 mol) and 33.4 g cobalt(II) bromide (0.15 mol) in 1500 ml water there were added at room temperature 283.5 g titanium-oxide powder (Norton). Then the mixture was made alkaline with diluted caustic soda solution. The suspension was drawn off by suction, washed and dried at 100° C. The catalyst contained 2.5% Pd and 3% Co, in each case reckoned as metal.

Use of the Supported Catalyst for the Production of Diphenyl Carbonate

Example 1 was repeated, whereby instead of 0.34 g palladium bromide use was made of 4 g of the heterogeneous catalyst produced above and working was effected at 8 bar.

The analyses showed that after one hour 6.5% diphenyl carbonate, after 2 hours 11.3% diphenyl carbonate and after 3 hours 15.6% diphenyl carbonate was contained in the reaction mixture. In the deep-freeze traps of the vacuum line 22.9 g of a phenol/water mixture were condensed.

EXAMPLE 7

Covering of a Titanium-Dioxide Extrudate with Palladium and Manganese 200 ml titanium-dioxide extrudate were steeped with 58.4 ml of a solution of 21.6 g manganese(II) chloride in water. Then drying was effected under nitrogen at 110° C. The support doped with manganese was steeped with 58 ml of a solution containing 33.3 g sodium tetrachloropalladate(II) solution with 15% palladium. Then drying was effected under nitrogen at 110° C. The finished contact substance contained 25 g Pd and 30 g Mn per liter, in each case reckoned as metal.

Use of the Supported Catalyst for the Production of Diphenyl Carbonate

The use of the supported catalyst for the production of diphenyl carbonate was effected as in Example 6, with the difference that the catalyst (12 ml) was located fixed in a wire-mesh basket.

The analyses showed that after one hour 5.6% diphenyl carbonate, after 2 hours 10.9% diphenyl carbonate and after 3 hours 14.1% diphenyl carbonate was contained in the reaction mixture. In the cold trap 20.7 g of a phenol/water mixture were condensed.

EXAMPLE 8

Covering of a Titanium-Dioxide Extrudate with Palladium, Copper and Molybdenum 200 ml titanium-dioxide extrudate were pre-steeped with 100 ml of 25% ammonia solution. Then the support was mixed with a solution consisting of 300 ml of 25% ammonia solution, 1.44 g palladium(II) chloride (0.008 mol), 2.76 g copper(II)-chloride-2-hydrate (0.016 mol) and 3.04 g ammonium molybdate(VI)-4-hydrate (0.0025 mol).

The mixture was rolled for 1 h at 80° C. and the volatile constituents were then removed in a vacuum at 80° C. After drying under nitrogen at 200° C. a catalyst was obtained which contained 4.3 g Pd, 5.2 g Cu and 8.3 g Mo per liter of contact mass.

Use of the Supported Catalyst for the Production of Diphenyl Carbonate

The use of the supported catalyst for the production of diphenyl carbonate was effected as in Example 6.

The analyses showed that after one hour 4.5% diphenyl carbonate, after 2 hours 6.8% diphenyl carbonate and after 3 hours 8.7% diphenyl carbonate was contained in the reaction mixture. In the cold trap 15.3 g of a phenol/water mixture were condensed.

EXAMPLE 9

Figure 4:
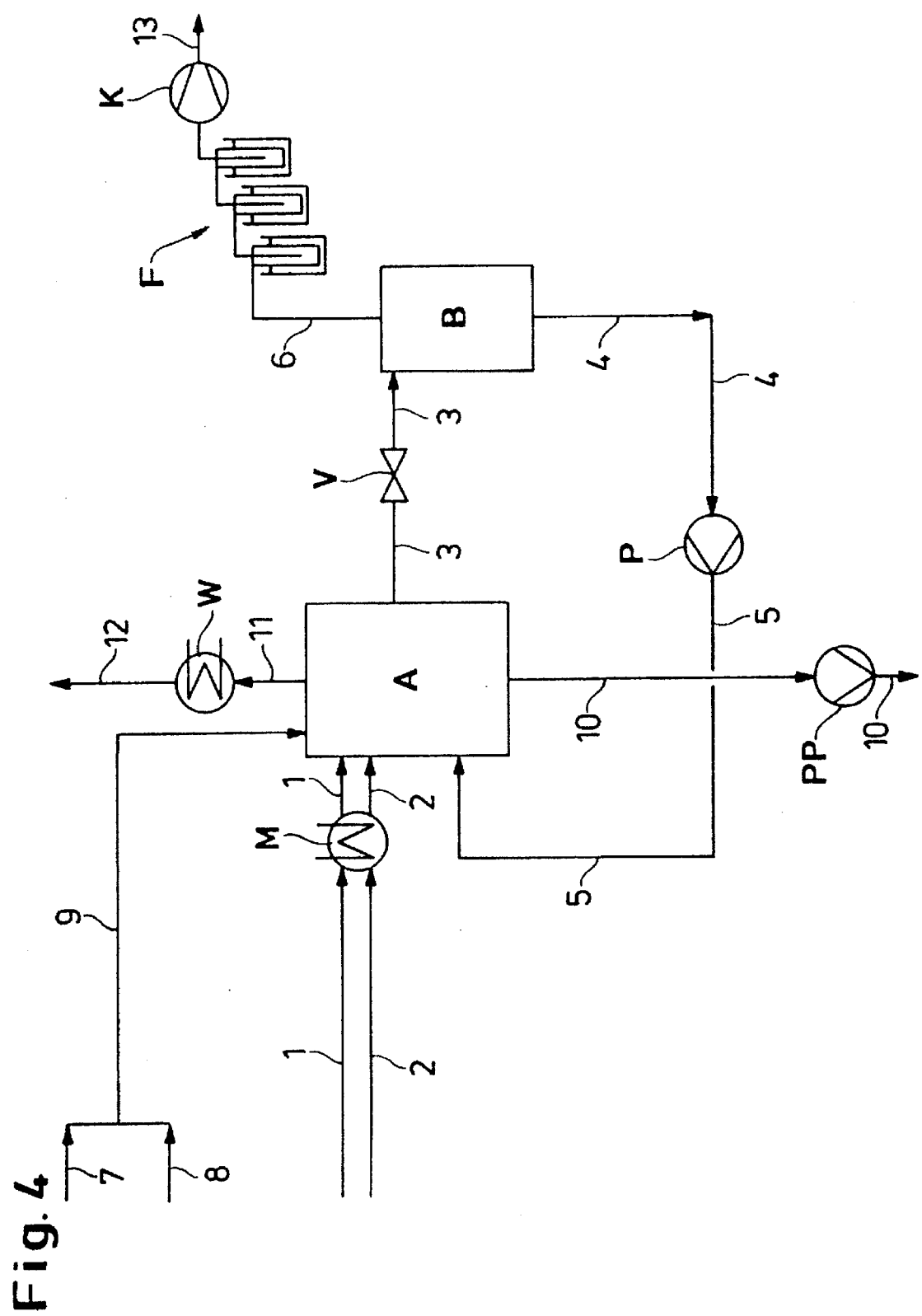

With the apparatus represented schematically in FIG. 4, consisting of a 1-1 autoclave (A), continuous dosing of gas and educt, continuous outward transfer of gas and liquid and also continuous withdrawal, treatment and feedback of partial flow, a continuous experiment was carried out.

Via line 1 and heater (M) an activated catalyst solution, consisting of 0.10 g palladium bromide, 8.31 g tetrabutyl ammonium bromide and 1.07 g manganese(III)-acetylacetonate in 450 g phenol, was conveyed into the reactor every hour. At the same time a sodium-phenolate solution, consisting of 2.21 g sodium phenolate, dissolved in 50 g phenol, was charged every hour via line 2 and heater (M).

Moreover, every hour about 200 ml of dehydrated reaction solution were returned via pump (P) and line 5.

The temperature of the reaction solutions amounted to 80° C. Into the reactor there were introduced every hour via the lines 7, 8 and 9, 100 Nl of a gaseous mixture consisting of carbon monoxide and oxygen (96.5:3.5 vol-%). The reactor pressure amounted to 10 bar and the internal temperature was regulated to 80° C. Excess reaction gas left the reactor via line 11, condenser (W) and line 12. The internal pressure of the reactor was maintained via a pressure gauge in line 9 and a control valve in line 12.

With the aid of a vertical pipe about 220 ml of reaction solution were withdrawn every hour via line 3 and the relief valve (V), lowered in pressure to about 100 mbar and dehydrated in the thin-layer evaporator (B) at 80° C. Evaporated phenol/water mixture was removed via line 6 and condensed in deep-freeze traps (F) (−78° C.) upstream of the vacuum pump (K). About 20–30 ml of mixture accumulated every hour in the cold traps (F).

The dehydrated reaction solution reached the reactor again via line 4, the valveless pump (P) and line 5.

Via line 10 about 500 ml of reaction solution were withdrawn every hour with the aid of the pump (PP). A sample was withdrawn every 1 hour from the reaction mixture that had been transferred outward and analysed by gas chromatography. After about 4 h the apparatus was in equilibrium. The analyses showed that 12% diphenyl carbonate was contained in the reaction solutions.

We claim:

1. A process for the production of an aromatic carbonate of the formula $$R-O-CO-O-R \qquad (I)$$

in which

R is selected from the group consisting of substituted or non-substituted $C_6$–$C_{12}$ aryl by reaction of an aromatic hydroxy compound of the formula $$R-O-H \qquad (II)$$

in which R has the significance specified above, with carbon monoxide and oxygen in fire presence of a platinum-group metal catalyst, a co-catalyst, a quaternary salt and a base at a temperature of 30° to 200° C. and a pressure of 1 to 200 bar, characterised in that the reaction water is continuously removed from a partial flow of the reaction solution under reduced pressure and largely isothermal conditions and the dehydrated partial flow is again supplied to the reaction.

2. A process according to claim 1, characterised in that the partial flow of reaction solution that is withdrawn per hour amounts to 0.01 to 30 times the contents of the reactor.

3. A process according to claim 1, characterised in that the evaporation of the water takes place in an apparatus selected from the group consisting of vertical-pipe, horizontal-pipe, slanting-pipe, rotor, thin-layer, centrifugal, worm, falling-film evaporators, tube-bundle evaporators, basket evaporators, evaporators with external return pipe and forced circulation, evaporators with external heating elements and forced circulation.

4. A process according to claim 1, characterised in that the temperature for dehydration of the partial flow lies within the range of ±30° C. of the reaction temperature.

5. A process according to claim 1 or 4, characterised in that all pipelines and evaporators are heated in such a way that the partial flow that is withdrawn remains at the temperature of the contents of the reactor.

6. Process according to claim 1, characterised in that the dehydration of the partial flow is carried out at a pressure of 1–5,000 mbar.

\* \* \* \* \*